United States Patent [19]

Michalczyk et al.

[11] 4,052,335

[45] Oct. 4, 1977

[54] CATALYST FOR THE PRODUCTION OF GAMMA-BUTYROLACTONE AND A METHOD FOR PREPARING THE CATALYST

[75] Inventors: Georg Michalczyk, Neukirchen-Vluyn; Karl-Heinz Gluzek, Alpen, both of Germany

[73] Assignee: Deutsche Texaco Aktiengesellschaft, Hamburg, Germany

[21] Appl. No.: 686,853

[22] Filed: May 17, 1976

Related U.S. Application Data

[62] Division of Ser. No. 583,363, June 4, 1975, Pat. No. 3,994,928.

[30] Foreign Application Priority Data

June 18, 1974 Germany .............................. 2429085

[51] Int. Cl.$^2$ .................. B01J 21/08; B01J 21/18; B01J 23/44; B01J 23/74

[52] U.S. Cl. .................. 252/446; 252/459; 252/460

[58] Field of Search .................. 252/446, 460, 459

[56] References Cited

U.S. PATENT DOCUMENTS

| | | | |
|---|---|---|---|
| 3,655,747 | 4/1972 | Sennewald et al. | 252/472 X |
| 3,883,444 | 5/1975 | Maselli et al. | 252/455 R |
| 3,926,853 | 12/1975 | Senes et al. | 252/460 X |

OTHER PUBLICATIONS

Handbook of Chemistry & Physics, 32nd Edition, pp. 1521-1522 (1950-1951).

*Primary Examiner* — W. J. Shine
*Attorney, Agent, or Firm* — Thomas H. Whaley; Carl G. Ries; George J. Darsa

[57] ABSTRACT

A process for the liquid-phase hydrogenation of maleic anhydride to γ-butyrolactone in the presence of a catalyst composed of cobalt oxide and palladium on a support of silica.

7 Claims, No Drawings

CATALYST FOR THE PRODUCTION OF GAMMA-BUTYROLACTONE AND A METHOD FOR PREPARING THE CATALYST

This is a division, of application Ser. No. 583,363, filed June 4, 1975, now U.S. Pat. No. 3,994,928, issued Nov. 30, 1976.

BACKGROUND OF THE INVENTION

The invention relates to a process for the production of a novel catalyst and to the hydrogenation of maleic anhydride in the liquid phase at an elevated pressure and temperature to produce γ-butyrolactone employing said catalyst.

Catalysts of multifarious compositions are available for the hydrogenation of maleic anhydride to γ-butyrolactone, Raney catalysts being the best known catalysts. However as taught by U.S. Pat. No. 2,772,292, Raney catalysts are highly pyrophoric and cannot be regenerated so that it has become increasingly the practice to use supported catalysts. The supported catalysts contain nickel as the catalytic component or cobalt in combination with a promoter, for example molybdenum or rhenium. While these supported catalysts are also pyrophoric, they can be stabilized by treatment with air diluted with carbon dioxide or a protective gas. The stabilizing treatment is, however, cumbersome and expensive. The supported catalysts have the additional disadvantage that their selectivity for γ-butyrolactone is not as high as would be desirable such that $C_3$ and $C_4$ alcohols and acids and their products of esterification are formed as by-products. The high by-product formation results in a reduced yield of γ-butyrolactone and the catalyst is irreversibly deactivated by the acids.

It is an object of the invention to provide a process for the hydrogenation of maleic anhydride to γ-butyrolactone in the liquid phase in high yields.

Another object of this invention is to provide a process for converting maleic anhydride to γ-butyrolactone in the presence of a novel selective and non-pyrophoric catalyst which does not require stabilization.

Yet another object of this invention is to provide a method for preparing a new catalyst useful in converting maleic anhydride to γ-butyrolactone where the catalyst is readily regenerable.

Other objects and advantages will become apparent from a reading of the following detailed description and examples.

DESCRIPTION OF THE INVENTION

Broadly, this invention contemplates a process for converting maleic anhydride to γ-butyrolactone which comprises contacting said anhydride in the liquid phase with hydrogen in the presence of a catalyst composed of cobalt oxide and palladium on a support of silica. In general, the process is conducted under elevated pressures and at elevated temperatures as for example temperatures in the range of from 20° to 400° C., preferably from 100° to 250° C. and under pressures suitably of from 50 to 350 kg/cm², preferably 100 to 150 kg/cm².

The novel catalyst of this invention comprises from 20 to 30 weight percent cobalt oxide 0.5 to 1.0 weight percent palladium on a silica support. The catalyst provided herein is non-pyrophoric and is prepared by impregnating a silica support with at least one solution of a decomposable salt of a catalytically active metal, drying the impregnated support, heating the impregnated support in air or in a nitrogen containing environment and decomposing the salt, and activating the catalyst in a hydrogen environment. More specifically, the method of preparing the catalyst is characterized by the following steps:

a. impregnating a silica support with a cobalt salt solution and drying said cobalt impregnated silica;

b. impregnating said dried cobalt impregnated silica support of (a) with palladium and drying said cobaltpalladium impregnated silica;

c. calcining said dried impregnated silica support of (b) at a temperature sufficient to decompose said cobalt salt to cobalt oxide; and d. activating said calcined support of (c) at a temperature of 400° to 500° C., preferably 420° to 480° C. in a hydrogen atmosphere.

It has surprisingly been found that a highly active cobalt catalyst which is non-pyrophoric, may be obtained if the support is dried after its impregnation with the cobalt salt solution, and is only then impregnated with palladium. However, if the silica support is impregnated simultaneously with the cobalt salt solution and palladium or with one solution after the other without intermediate drying, a catalyst is obtained which is pyrophoric. The essential feature of the invention thus resides in the observation of a specific order of succession in which the solutions of the catalytically active metals are applied and the drying between the applications of the cobalt salt solution and of the palladium. It has been found that the combination of cobalt and palladium has a synergistic effect. Moreover, since the catalysts of this invention are not pyrophoric, stabilization of the same is entirely superfluous.

Commercially available kieselguhr or commercially avaiable $SiO_2$ in the form of granules or pellets having an average diameter of about 1.5 to 3.5 mm., preferably from 2 to 3 mm. may serve as the $SiO_2$ support. Any such pre-formed $SiO_2$ used should be degassed and dried in vacuo at an elevated temperature before it is impregnated with the cobalt salt solution. Fifteen minutes drying at 80°-90° C. is generally sufficient.

The cobalt salt solution is a solution of a cobalt salt which is decomposable when heated, for example the nitrate, the formate, the acetate or the salt of another volatile organic acid.

The palladium can also be introduced in the form of a solution of a salt which is decomposable by reduction; palladium chloride is the least expensive and is thus the preferred salt. The palladium may also be introduced in the form of palladium on carbon (10% by weight of palladium deposited on 90% by weight of activated carbon) which is then admixed with the supporting material impregnated with cobalt.

The $SiO_2$ support, the cobalt salt solution and the palladium, that is to say, the palladium salt solution or palladium deposited on activated carbon, are used in amounts sufficient to produce a catalyst of the following average composition:

from 20% to 30% by weight of CoO from 0.5% to 1% by weight of Pd, the balance bringing the total to 100% by weight being $SiO_2$.

Solutions of the highest possible concentration, that is to say, solutions ensuring a good impregnation facilitating thorough kneading of the mass are preferably used. Higher dilutions, while having no detrimental effect upon the activity of the catalyst, necessitate, however, a prolonged drying, whilst the use of highly concentrated solutions involves extended mixing periods. A little water is added where palladium deposited on activated carbon is used so that a kneadable mass may be obtained.

The drying after the impregnation with the cobalt salt solution may be carried out at a temperature up to 110° C. under atmospheric pressure or in vacuo at correspondingly lower temperatures. It has been found that the best results are obtained when the drying step is carried out at a temperature of about 80° C. within about one hour in a vacuum of 14 Torr.

In accordance with the invention, the second metallic component of the catalyst namely the palladium, is incorporated in the $SiO_2$ support laden with Co after the drying step by admixing a palladium salt solution or palladium deposited on carbon and a small amount of water in the manner hereinbefore described. The mass so obtained is then thoroughly kneaded during which the palladium component is absorbed on the surface of the catalyst impregnated with cobalt salt. This is followed by drying in vacuo at about 100° to 120° C., suitably 110° C., for a few hours, for example for one day, preferably for from 10 to 12 hours, and, finally, decomposition of the cobalt salt and of the palladium salt when employed by thermal treatment in air or nitrogen and subsequent activation of the crude catalyst by heating in a hydrogen atmosphere. In the process according to the invention, the decomposition is carried out at a temperature of 400° to 500° C., preferably 420° to 480° C., for 1.5 – 5 hours and in a highly preferred embodiment at 450° C. for three hours, at a rate of flow of the nitrogen of from 20 to 30 liters, preferably 25 liters, per hour. The activation of the catalyst is carried out at a temperature of from 400° to 500° C., preferably 420° to 480° C., for a period of from 1.5 to 5 hours and in a highly preferred embodiment at 450° C. for a period of three hours, at a rate of flow of the hydrogen of from 20 to 30 liters, preferably at a rate of 25 liters per hour. It will be understood that the rates of flow of the gas most suitable at the time depend upon the conditions under which the treatments are carried out, such as the depth of layer or the movement of the catalyst, the size of the batch, the size of the vessel, and the like.

The catalyst obtained by the process according to the invention is distinguished by the fact that it is non-pyrophoric and need not be subjected to a special stabilizing treatment. It is obtained in the form of a black, loose powder, or in the form of lustrous, black globules or granules according to the form of the $SiO_2$ support charged. The catalyst is particularly suitable for the hydrogenation of maleic acid anhydride to γ-butyrolactone in the liquid phase. The hereinafter given Examples 5 to 8 and Table II connected therewith show that a 100% conversion of maleic anhydride is obtained with a very high yield of γ-butyrolactone. The pulverulent catalyst is predominantly suitable for batchwise operation, catalysts in spherical form being advantageously used for continuous operation by reason of their high mechanical stability.

The catalyst according to the invention has a very long useful life. It has still its full activity even after 1000 hours of continuous operation. The catalyst may, moreover, be very easily regenerated by passing air over it followed by a treatment with hydrogen.

According to a preferred embodiment of the process of this invention, hydrogen is introduced to a reactor containing maleic anhydride at a pressure of from 100 to 150 kg/cm², the temperature is raised to 100° to 250° C. within 2 hours, and subsequently the reaction is allowed to continue for 2 more hours. Shorter or longer periods of time can also be employed. While the amount of catalyst employed in the reaction can vary over a broad range, we employ from about 0.1 to 100, preferably about 5 to 20, parts by weight of the cobalt oxide-palladium on silica catalyst per 100 parts by weight of maleic anhydride. In contrast to other processes for converting maleic anhydride to γ-butyrolactone which are conducted in the gaseous phase, the process of our invention is carried out in the liquid phase which is a great advantage with regard to conversion and reactor dimensions. The catalytic process can be conducted in a wide range of solvents inert to the reaction as, for example, aliphatic alcohols such as methanol, ethanol, butanol and higher alcohols; aromatics such as benzene, toluene or xylene; dimethylformamide; and cyclic ethers such as tetrahydrofuran or tetrahydropyran. A particularly preferred solvent for converting maleic anhydride is γ-butyrolactone which is the compound that emerges as the end product of the process and this need not be removed. Whether γ-butyrolactone or another solvent is used in the course of the reaction, the results are the same. In general, the maleic anhydride concentration in the solvent can vary from 25 to 75 weight percent. When γ-butyrolactone is employed as solvent about 50 percent solutions are most convenient. In the instance where Γ-butyrolactone is intended to be converted to tetrahydrofuran in a further stage, the reaction solvent for the maleic anhydride in such a case is preferably tetrahydrofuran.

The product of the instant process, γ-butyrolactone, has utility as a solvent and as a thinner for paints and lacquers. In addition, γ-butyrolactone is useful as an intermediate in the production of tetrahydrofuran.

The invention and the advantages obtained thereby are illustrated in the following Examples.

EXAMPLES 1 to 4

In these Examples catalysts according to the invention in pulverulent form were produced.

Commercially available kieselguhr was impregnated with a cobalt nitrate solution and the water was evaporated in vacuo. A palladium chloride solution or palladium deposited on activated carbon was then added, the mass was kneaded and thus thoroughly mixed and subsequently dried in vacuo at 110° for 10 hours followed by grinding the lumpy material to a fine powder. The powder so obtained was heated for three hours in a current of nitrogen (rate of flow 25 liters per hour) to a temperature of 450° C. to decompose the nitrate, and the crude catalyst was activated for three hours in a hydrogen current (rate of flow: 25 liters per hour) at the same temperature.

The quantities in which the individual starting materials were used in the different Examples are shown in Table I.

In all of the four Examples, the catalysts were obtained in the form of a loose, non-pyrophoric, black powder.

EXAMPLES 5 to 7

In these Examples the catalysts according to the invention were obtained in the form of small spheres or pellets.

Commercially available $SiO_2$ spherical pellets from 2 to 3 mm. in diameter, were dried in vacuo at a temperature of 80° C. for 15 minutes. This was followed by impregnation with a cobalt nitrate solution and evaporation of the water in vacuo. A palladium chloride solution was then added followed by thorough mixing and drying in vacuo at 110° C. for 10 hours. The decomposition of the nitrate and the activation of the crude catalyst were carried out as described in Examples 1 to 4. The quantities in which the individual starting materials in Examples 5 to 7 were used are also shown in Table I.

In all of the three Examples, the catalysts were obtained in the form of lustrous, black non-pyrophoric spheres or pellets.

placed in communication with the autoclave. When a constant pressure was reached in the autoclave, the temperature was increased to 250° C. and fresh hydrogen at 150 atmospheres pressure was again added until a constant pressure was reached again.

After removal of the excess pressure, the product was separated from the catalyst and subjected to gas chromatographic analysis with reference to diethyl ketone as a standard.

The following Table II gives particulars of the individual Examples, including the quantities of maleic anhydride and of solvent γ-butyrolactone used, and the

TABLE I

| Catalyst according to Example No. | Production of the catalysts in Examples 1 to 7 | | | |
|---|---|---|---|---|
| | $SiO_2$ | $Co(NO_3)_2 \cdot 6 H_2O$ | $PdCl_2$ | pd/C |
| 1 | Kieselguhr, 79g | 77.6g | 1.67g in 100 ml in $HNO_3$ | — |
| 2 | Kieselguhr, 70g | 77.6g in 100 ml. $H_2O$ | — | 10Pd on activated carbon (10%) |
| 3 | Kieselguhr, 74g | 97.1g | 6.67g (containing 15% Pd) in 50 ml. $H_2O$ | — |
| 4 | Kieselguhr, 69g | 116.6g | " " | — |
| 5 | Spherical pellets 2-3 mm 395g | 388g in 300 ml. | 16.7g (containing 15% Pd) in 200 ml. $H_2O$ | — |
| 6 | " 124.5g | 121.2g in 100 ml. $H_2O$ | 7.9g (containing 15% Pd) in 50 ml. $H_2O$ | — |
| 7 | " 603g | 788g in 750 ml. $H_2O$ | 53.6g (containing 15% Pd) in 500 ml. $H_2O$ | — |

The catalysts obtained in Examples 1 to 7 were tested in nine tests (Examples 8 to 16) for their suitability as catalysts for the hydrogenation of maleic anhydride to γ-butyrolactone.

catalyst quantity of it used in each case. The results of the analysis of the product are also shown in Table II.

TABLE II

| Hydrogenation of maleic anhydride to Γ-butyrolactone using the catalysts produced in Examples 1 to 6 | | | | | | | | | | |
|---|---|---|---|---|---|---|---|---|---|---|
| Catalyst | | | Quantity of MSA charged g/g GBL | Composition of the hydrogenation product wt.% | | | | | MSA conversion % | GBL selectivity % |
| Example No. | Example No. | Quantity grams | | THF | GBL | BSE | $H_2O$ | Others | | |
| 8 | 1 | 20 | 200/200 | 3.2 | 86.2 | | 8.1 | 2.5 | 100 | 88.5 |
| 9 | 1 | 40 | 200/200 | 4.1 | 86.3 | 0.2 | 8.7 | 0.7 | 100 | 88.7 |
| 10 | 2 | 30 | 300/300 | 3.1 | 85.6 | | 8.3 | 3.0 | 100 | 87.0 |
| 11 | 3 | 20 | 200/200 | 5.2 | 84.1 | 1.8 | 8.6 | 0.3 | 100 | 83.5 |
| 12 | 4 | 20 | 200/200 | 4.0 | 86.4 | 0.8 | 8.0 | 0.8 | 100 | 89.0 |
| 13 | 5 | 20 | 200/200 | 0.7 | 88.0 | | 7.9 | 3.0 | 100 | 92.6 |
| 14 | 6 | 20 | 200/200 | 4.1 | 86.5 | 0.2 | 9.2 | 0 | 100 | 89.3 |
| 15 | 6 | 27 + 3 g Pd/C (5% Pd) | 300/300 | 2.2 | 88.2 | 0.5 | 8.6 | 0.5 | 100 | 93.2 |

MSA maleic anhydride
BSE butyric acid
GBL Γ-butyrolactone
$H_2O$ water formed during the reaction
THF tetrahydrofuran
"Others" constituents not analysed

EXAMPLES 8 to 15

An autoclave provided with a stirrer, a gas inlet tube and a gas outlet tube was charged with the maleic anhydride to be hydrogenated, the solvent γ-butyrolactone and the catalyst. The autoclave was then flushed, twice with nitrogen and once with hydrogen, and was then closed and heated to 100° C. When this temperature was reached, hydrogen at 150 atmospheres pressure was

EXAMPLES 16 to 18

The conditions under which these Examples were carried out were similar to those used in Examples 8 to 15 except that tetrahydrofuran instead of γ-butyrolactone served as the solvent.

Particulars of the three Examples and the results obtained are shown in Table III.

TABLE III

| Hydrogenation of maleic anhydride to gamma-butyrolactone using the catalysts produced according to Examples 1, 2 and 7 | | | | | | | | | | |
|---|---|---|---|---|---|---|---|---|---|---|
| Catalyst | | | Quantity of MSA charged g/g THF | Composition of the hydrogenation product Wt.% | | | | | MSA conversion % | GBL selectivity % |
| Example No. | Example No. | Quantity grams | | THF | BSE | GBL | $H_2O$ | Others | | |
| 16 | 1 | 20 | 200/200 | 50.8 | 1.5 | 38.7 | 8.0 | 1.0 | 100 | 90.8 |
| 17 | 2 | 20 | 200/200 | 49.9 | 0.5 | 40.9 | 8.0 | 0.7 | 99 | 96.2 |
| 18 | 7 | 20 | 200/200 | 49.2 | 0.9 | 40.1 | 8.3 | 1.5 | 100 | 94.0 |

In the following Examples of Comparison A and B, a cobalt catalyst and a palladium catalyst, respectively, were prepared and their suitability for converting maleic anhydride to γ-butyrolactone was tested.

EXAMPLE OF COMPARISON A

A catalyst was prepared from 80 grams of kieselguhr and 77.6 grams of cobalt chloride-hexahydrate, as described in Examples 1 to 4, with the exception of the addition of palladium chloride solution or of palladium deposited on activated carbon.

200 grams of maleic anhydride and 200 grams of γ-butyrolactone were hydrogenated at a temperature of 250° C and at a hydrogen pressure of 150 atmospheres in the presence of 20 grams of the catalyst described above until a constant pressure was reached (as described in Examples 8 to 15).

The hydrogenation product had the following composition (in percent by weight):

| | | |
|---|---|---|
| | THF | 0.9 |
| | GBL | 62.3 |
| | BSE | 0.5 |
| | $H_2O$ | 7.0 |
| | others | 29.3 |
| | MSA conversion | 100 |
| | GBL selectivity | 32.4 |

EXAMPLE OF COMPARISON B 200 grams of maleic anhydride in 200 grams of γ-butyrolactone were hydrogenated in the presence of 20 grams of a commercially available palladium/kieselguhr catalyst (10 percent by weight of Pd), as described in Example A.

The hydrogenation product comprises the following composition (in percent by weight):

| | | |
|---|---|---|
| | THF | 0.1 |
| | GBL | 60.9 |
| | BSE | 1.8 |
| | $H_2O$ | 3.0 |
| | others | 34.2 |
| | MSA conversion | 100 |

-continued

| | | |
|---|---|---|
| | GBL selectivity | 32.4 |

In comparing the Examples 8 to 15 with the Examples of Comparison A and B with respect to the γ-butyrolactone in the hydrogenation products and the Examples 8 to 17 with the Examples of Comparison A and B with respect to the selectivity of γ-butyrolactone, the synergistic effect of the combination of cobalt and palladium showed clearly.

We claim:

1. A catalyst consisting of cobalt oxide and palladium on silica, wherein said catalyst comprises from about 20 to 30 percent cobalt oxide and from 0.5 to 1.0 weight percent palladium.

2. A method of preparing a cobalt oxide and palladium on silica catalyst which comprises
   a. impregnating a silica support with a cobalt salt solution and drying said cobalt impregnated silica;
   b. impregnating said dried cobalt impregnated silica support of (a) with palladium and water or a palladium salt solution and drying said cobalt-palladium impregnated silica;
   c. calcining said dried silica support of (b) at a temperature sufficient to decompose said cobalt salt to cobalt oxide and
   d. activating said calcined support of (c) at a temperature of 400° to 500° C. in a hydrogen atmosphere.

3. A method according to claim 2 wherein said calcining in (c) is conducted at a temperature of 400° to 500° C.

4. A method according to claim 2 wherein said calcining in (c) is conducted in nitrogen at a temperature of 420° to 480° C.

5. A method according to claim 2 wherein said activating in (d) is conducted at a temperature of 420° to 480° C.

6. A method according to claim 2 wherein said dried cobalt impregnated silica support in (b) is impregnated with a palladium salt solution.

7. A method according to claim 2 wherein said dried cobalt impregnated silica support in (b) is impregnated with palladium by contacting with palladium deposited on carbon and water.

* * * * *